Figure 1:
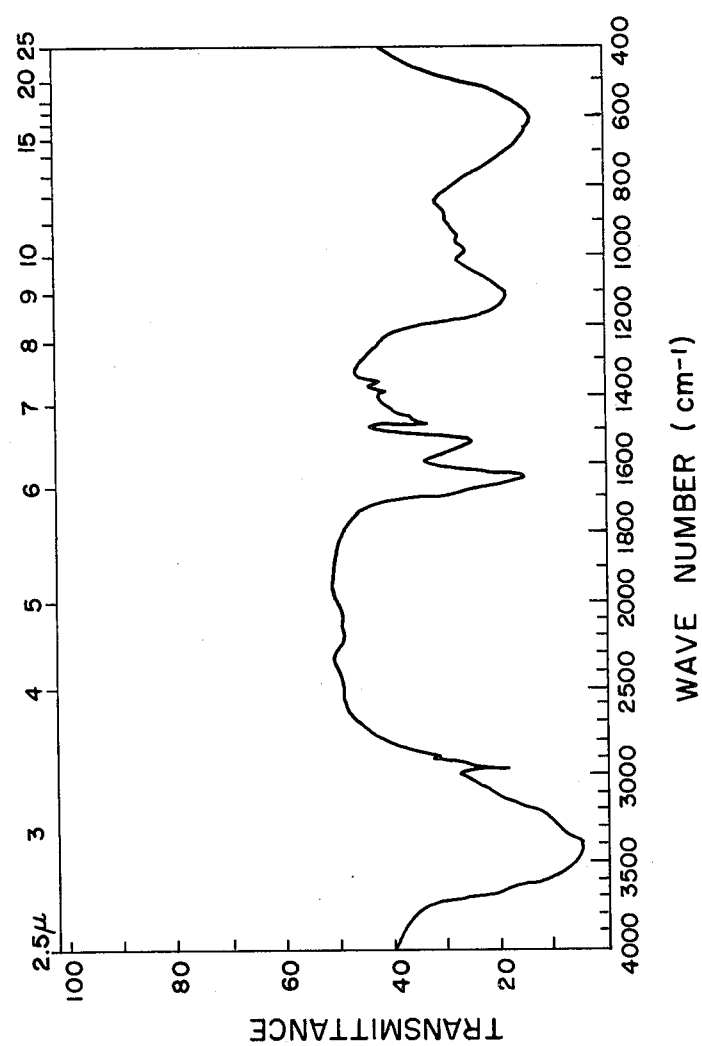

United States Patent

Kojima et al.

[11] 4,348,386
[45] Sep. 7, 1982

[54] PROTEASE INHIBITORS

[75] Inventors: Shinichi Kojima, Ashiya; Ten Koide, Takarazuka; Shigeo Ogino, Nishinomiya; Toshiro Tsuchiya; Yoshito Kameno, both of Minoo, all of Japan

[73] Assignee: Sumitomo Chemical Company, Limited, Osaka, Japan

[21] Appl. No.: 249,984

[22] Filed: Apr. 1, 1981

[30] Foreign Application Priority Data

Apr. 16, 1980 [JP] Japan ................................. 55-50725

[51] Int. Cl.³ ..................... A61K 37/00; C07C 103/52
[52] U.S. Cl. .............................. 424/177; 260/112.5 R
[58] Field of Search .................. 424/177; 260/112.5 R

[56] References Cited

PUBLICATIONS

Holm, et al., "Inhibition of Gastric Peptic Activity", pp. 119-121, 1976.
Berstad, et al., "Experience wtih Antipeptic Agents", pp. 121-123, 1979.
Svendsen, et al., Gastric Ulcer Theraphy with a Pepsin Inactivating, pp. 929-932, 1979.

Primary Examiner—Delbert R. Phillips
Attorney, Agent, or Firm—Cushman, Darby & Cushman

[57] ABSTRACT

An acidic protease inhibitor obtained by allowing a compound of

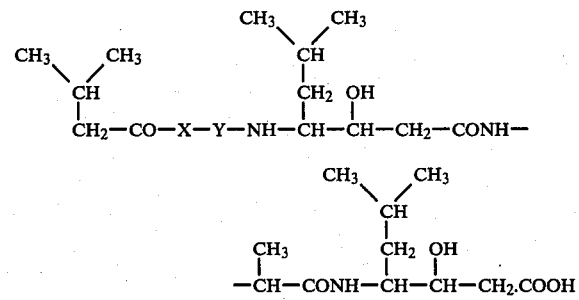

wherein X and Y are L-leucine or L-valine, or its salt, to react with an aluminum compound in a medium containing water and/or an alcohol, and further continuing the reaction after adjusting the pH of the system within a range of 4.5 to 7. The protease can stay long in stomach, have an action to protect ulcerated areas and retain the antiulcer effect for a long period of time.

23 Claims, 7 Drawing Figures

PROTEASE INHIBITORS

The present invention relates to acidic protease inhibitors obtained by allowing a compound of the formula (I),

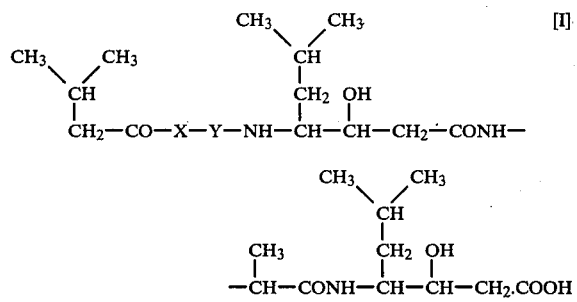

wherein X and Y are L-leucine or L-valine, or its salt to react with an aluminum compound in a medium containing water and/or an alcohol, and further continuing the reaction after adjusting the pH of the system to within a range of 4.5 to 7, their production and anti-ulcer agents containing at least one of them as an active ingredient.

The acidic protease inhibitors according to the present invention are characterized in that they stay long in stomach, have an action to protect ulcerated areas, and retain the anti-ulcer effect for a long time.

The compound of the formula (I) is a protease inhibitor produced by microorganisms, and it is well known that the biological activity of the compound is to uniquely inhibit the function of pepsin, renin [Japanese Pat. Nos. 8996/1972, 35759/1977 and 7517/1978, Biochemical Pharmacology, Vol 21, 2941–2944 (1972)]. It is said that gastric pepsin acts as aggresive factor to take part in ulcer formation and the process thereof.

It is in fact well known that, in gastric ulcer models with animals, the anti-pepsin agent represented by the formula (I) exhibits very good therapeutic effects on acute ulcers including Shay ulcer when administered orally. But the compound of the formula (I) is poor in the effect on chronic ulcers.

As a result of extensive study with the compound of the formula (I) as starting material, the inventors found an acidic protease inhibitor which is effective for not only acute ulcers including Shay ulcer but also ulcers considered as chronic ones. That is, it became clear for the first time that the acidic protease inhibitor, obtained as precipitates by allowing a compound of the formula (I) or its salt to react with an aluminum compound in a medium containing water and/or an alcohol, followed by reaction at a pH of 4.5 to 7, has both the anti-pepsin action and antacid action as well as good therapeutic effect on chronic ulcers.

In the accompanying drawings, FIGS. 1 to 7 show IR spectrums of compounds obtained in Examples 1 to 7, respectively.

The substance according to the present invention is generally produced by dissolving the compound of the formula (I) in a suitable medium, adding to the resulting solution a solution of an aluminum compound in water or an alcohol (e.g. methanol, ethanol) to bring the compounds into reaction, and then further continuing the reaction after adjusting the pH of the system to within a range of 4.5 to 7.

The medium used for dissolving the compound of the formula (I) includes for example water, alcohols (e.g. methanol, ethanol, n-propanol, isopropanol, n-butanol), dimethyl sulfoxide and dimethylformamide which may contain water. Of these, alcohols particularly methanol are preferred. It is further desirable to add an alkali agent such as sodium hydroxide, potassium hydroxide, ammonium hydroxide or the like.

As the aluminum compound, there may be given for example chlorinated aluminum compounds (e.g. aluminum chloride, basic aluminum chloride), organo-aluminum compounds [e.g. aluminum tri-sec-butoxide [(sec-$C_4H_9O)_3Al$], aluminum triisopropoxide [(iso-$C_3H_7O)_3Al$], aluminum monoisopropoxy di-sec-butoxide [(iso-$C_3H_7O$)(sec-$C_4H_9O)_2Al$]]. Of these compounds, those containing aluminum chloride or basic aluminum chloride as a main component are preferred. Basic aluminum chloride is easily prepared by the well-known methods, for example, by allowing metallic aluminum or aluminum hydroxide to react with hydrochloric acid, or by treating aluminum chloride with sodium hydrogen carbonate. Various kinds of commercially available basic aluminum chloride also may be used. Further, these aluminum compounds may contain 0 to 5% of $SO_4^{--}$ as a stabilizer. The amount of the aluminum compound used is generally 0.05 to 20 times by weight, preferably 0.1 to 10 times by weight, more preferably 0.1 to 5 times by weight, as converted to alumina ($Al_2O_3$), based on the compound [I].

Preferably, the solution of the aluminum compound is gradually added with stirring. After addition, the pH of the system is gradually adjusted to 4.5 to 7, preferably 6.8, with an aqueous alkali solution. This reaction is preferably carried out at not higher than 80° C.

The alkali may be any of those not disturbing the reaction, and it includes, for example, sodium hydroxide, potassium hydroxide, sodium carbonate, sodium hydrogen carbonate, potassium carbonate, potassium hydrogen carbonate and ammonium hydroxide. Of these compounds, ammonium hydroxide and sodium hydroxide are preferred.

On carrying out the reaction in such a manner, the reaction product is obtained as precipitate and recovered by filtration or centrifugation. For facilitating the recovery of the precipitate, solvents freely miscible with water such as alcohols and acetone may be used. The obtained precipitate is suspended in water or aqueous solvents to wash and then dried.

As is frequently encountered with aluminum compounds, there are no suitable dissolving solvents for the precipitate thus obtained. Since the precipitate is hardly soluble in water, organic solvents, dimethyl sulfoxide, dimethylformamide and the like, application of the general physicochemical analysis is difficult. Consequently, the chemical structure of the precipitate can not be clarified, but elementary analysis shows that the precipitate contains 12 to 75% of a substance derived from the compound of the formula (I) and 5 to 30% of aluminum.

On measuring the anti-pepsin activity of this precipitate, $ID_{50}$ was found to be within a range of 0.05 to 0.1 μg, and therefore this precipitate, even as such, has a sufficient anti-pepsin activity. While, it is said that aluminum hydroxide gel referred to in Japanese Pharmacopeia generally neutralizes gastric pepsin by its antacid power, and the action of anti-ulcer agents also is regarded as essentially due to the antacid power. On examining the antacid power of the acidic protease inhibitor according to the present invention, it was found that the power was 70 to 225 ml/g.

The acidic protease inhibitor of the present invention is, needless to say, produced using the compound of the formula (I) as starting material, as described above. Hereupon, the compound of the formula (I) is a pentapeptide having an acyl group at the terminal nitrogen atom of the peptide. Consequently, it may easily be presumed that the method of the present invention can also be applied to compounds having an acetyl, propionyl, isopropionyl, n-butyryl, n-caproyl, n-capryl group or the like in place of the acyl group.

The acidic protease inhibitor according to the present invention has no toxicity at all at a dosage of 4000 mg/kg when orally administered to mice and rats. Consequently, this inhibitor is of very low toxicity.

Thus, the acidic protease inhibitor of the present invention are useful as anti-ulcer agent. They can be administered orally to warm-blooded animals in the form of conventional pharmaceutical preparations.

A preferred dosage form includes tablets, capsules, granules, powders, liquids and the like. When the dosage form is of solid, carriers such as starch, sucrose, lactose, dicalcium hydrogen phosphate, barium sulfate, talc, stearic acid, magnesium stearate and gums are preferably used for preparation. When the dosage form is a capsule, there may also be given capsules packed with the active ingredients in admixture with a diluent or adjuvant agent, or as absorbed in gelatin or the like. Preferred liquids include for example emulsifiers, suspensions and syrups containing water and liquid paraffin. As vehicles for liquids, wetting agents, emulsifiers and suspending agents, for example vegetable oils eatable such as olive oil, sesame oil, peanut oil, linseed oil and sunflower oil can be used. Further, in any of the dosage forms, sweetening agents, taste-masking agents and flavors may be added.

Generally, the amount of active ingredient per unit dose is 50 mg to 1000 mg, and the dosage/day of active ingredient is varied from 100 mg to 3000 mg depending upon the degree of ulcer and the age of patients.

The present invention will be illustrated specifically with reference to the following examples, which are not however to be interpreted as limiting the invention thereto.

EXAMPLE 1

A compound of the formula (I) wherein both X and Y are L-leucine (10.4 g) was suspended in water (2.0 liters), and after adding 3.0 N sodium hydroxide (4.77 ml) thereto, it was dissolved by heating. Thereafter, an aqueous basic aluminum chloride solution, prepared by gradually adding sodium hydrogen carbonate (14.7 g) to a solution of aluminum chloride hexahydrate, $AlCl_3 \cdot 6H_2O$, (28.2 g) in water (243 ml), was added dropwise thereto. After 30 minutes' reaction at room temperature, 1% aqueous ammonia (263 ml) was gradually added to adjust the pH to 5.7, followed by 30 minutes' reaction at room temperature. The produced gel-form precipitate was separated by centrifugation, washed with three 800-ml portions of deionized water, and freeze-dried to obtain 19.0 g of a white powder. This compound obtained was measured for the pepsin inhibiting activity by the following method.

To a solution comprising a 0.6% casein solution (1.0 ml) obtained by dissolving Hammarsten's casein (produced by Wakō Junyaku Co.) in 0.08 M lactic acid solution, a 0.02 M hydrochloric acid/potassium chloride buffer solution having a pH of 2.2 (0.7 ml) and a sample solution (0.2 ml) was added a 40 µg/ml pepsin solution (0.1 ml). After carrying out reaction at 37° C. for 30 minutes, the reaction was stopped with addition of a 5% trichloroacetic acid (2.0 ml). The supernatant liquor obtained by centrifugation was measured for absorbance at 280 nm. In this test method, the amount of sample required for inhibiting the activity of crystalline pepsin (4 µg) by 50% was taken as $ID_{50}$.

The antacid power was measured according to the method of Japanese Pharmacopeia IX as follows: To a test sample (0.2 g) was added 0.1 N hydrochloric acid (100 ml), and the mixture was sealed air-tight, shaken at 37° C. for 1 hour and then filtered. Excessive hydrochloric acid in the filtrate (50 ml) was titrated with 0.1 N sodium hydroxide using Bromophenol Blue as indicator, and the amount of 0.1 N hydrochloric acid consumed per gram of the sample was taken as the antacid power.

The anti-pepsin effect, $ID_{50}$, of this compound was 0.07 µg, and this compound showed an antacid power to consume 135 ml of 0.1 N hydrochloric acid per gram.

Elementary analysis showed that this compound contained 43.7% of a compound derived from the compound of the formula (I) wherein both X and Y are L-leucine. The aluminum content of this compound was 14.7%, as measured by atomic absorption analysis. FIG. 1 shows the IR spectrum of this compound.

EXAMPLE 2

A compound of the formula (I) wherein both X and Y are L-valine (60.0 g) was suspended in water (12 liters), and after adjusting the pH to 7.5 with 3.0 N sodium hydroxide, it was dissolved by heating to 50° C. Thereafter, an aqueous basic aluminum chloride solution, prepared by gradually adding sodium hydrogen carbonate (88.3 g) to a solution of aluminum chloride hexahydrate, $AlCl_3 \cdot 6H_2O$, (169.2 g) in water (584 ml), was added dropwise thereto. The pH of the mixed solution was then adjusted to 5.1 with 4% aqueous ammonia, followed by 30 minutes' stirring at room temperature. The produced gel-form precipitate was collected by filtration, washed with a deionized water (1.5 liters), methanol (0.5 liter) and then with acetone (0.5 liter), and freeze-dried to obtain 103.4 g of a white powder.

The pepsin inhibiting activity and antacid power of this compound were measured by the methods described in Example 1 to obtain the following results: Pepsin inhibiting activity ($ID_{50}$), 0.07 νg; antacid power, 136 ml of 0.1 N HCl per gram.

Figure 2:
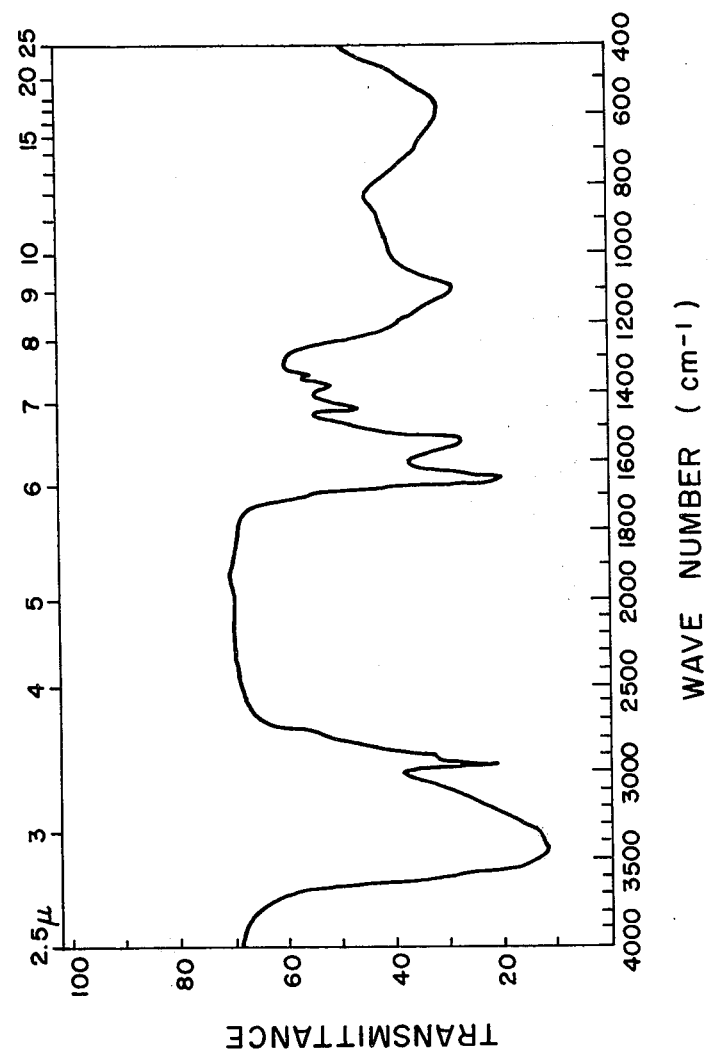

The composition of this compound was as follows: Content of a compound derived from the compound of the formula (I) wherein both X and Y are L-valine, 46.0%; and aluminum content, 15.3%. FIG. 2 shows the IR spectrum of this compound.

EXAMPLE 3

A compound of the formula (I) wherein both X and Y are L-valine (100 g) was placed in a 10-liter glass reactor together with methanol (6.4 liters) of 45° C., and dissolved with stirring. A 3 N sodium hydroxide solution (48.7 ml) was added, and the resulting solution was cooled with ice water. Separately from this, methanol (1.3 liters) was taken in a 3-liter glass beaker and cooled with ice water from the outside. Anhydrous aluminum chloride (194.4 g) was gradually added thereto with stirring while continuing the cooling, and then water (0.6 liter) was added. This aluminum chloride/methanol/water mixed solution was gradually added to the above solution, followed by 1 hour's stirring at room temperature. A 3 N aqueous sodium hydroxide solution (1000 ml) was then added dropwise with stirring to adjust the pH to 6.8, followed by standing overnight at room temperature. From the reaction solution containing precipitate was removed methanol under reduced pressure, and the solution was further concentrated to 2 liters. To this concentrated liquor was added water (4 liters), followed by 1 hour's stirring at room temperature for completion of gelation. The gel-form precipitate was collected on filter paper on Nutsche by vacuum filtration. The precipitate was washed with methanol (2 liters) and then with water until chlorine ions in the filtrate were no longer detected by the silver nitrate test, followed by dehydration with acetone (1 liter) and drying. Thus, 127 g of a compound was obtained. The antacid power and the pepsin inhibiting activity of this compound were measured according to the method described in Example 1 to obtain the following results: Antacid power, 102 ml of 0.1 N HCl per gram; and pepsin inhibiting activity ($ID_{50}$), 0.06 μg.

Figure 3:
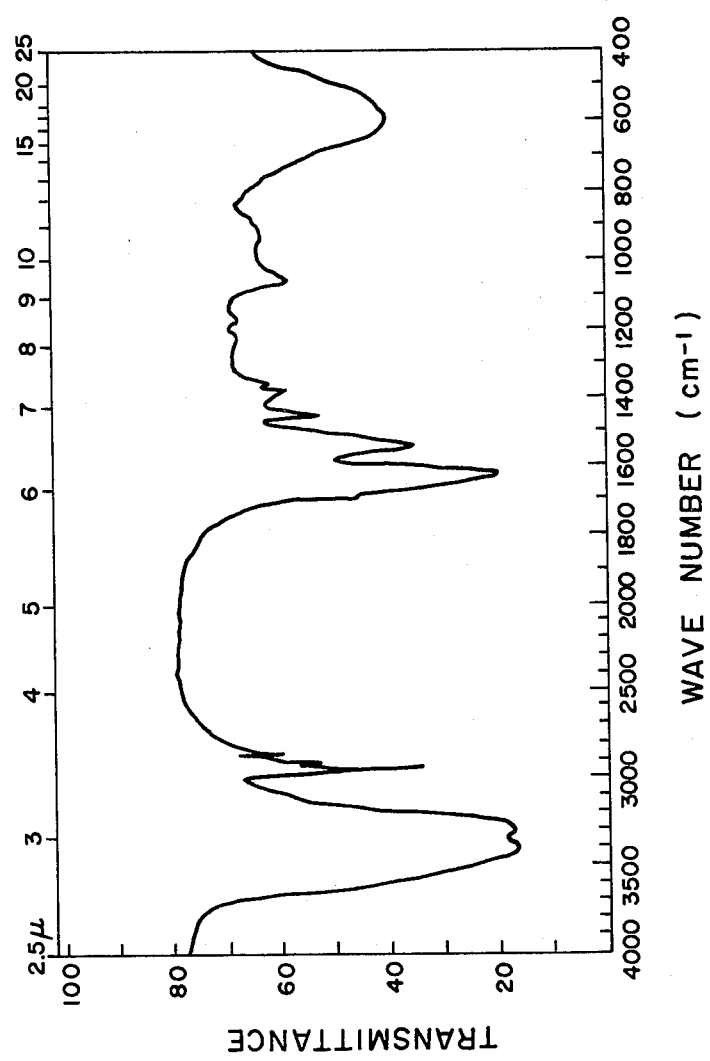

This compound had the following composition: Content of a compound derived from the compound of the formula (I), 37.8%; and aluminum content, 9.7%. FIG. 3 shows the IR spectrum of this compound.

EXAMPLE 4

Figure 4:
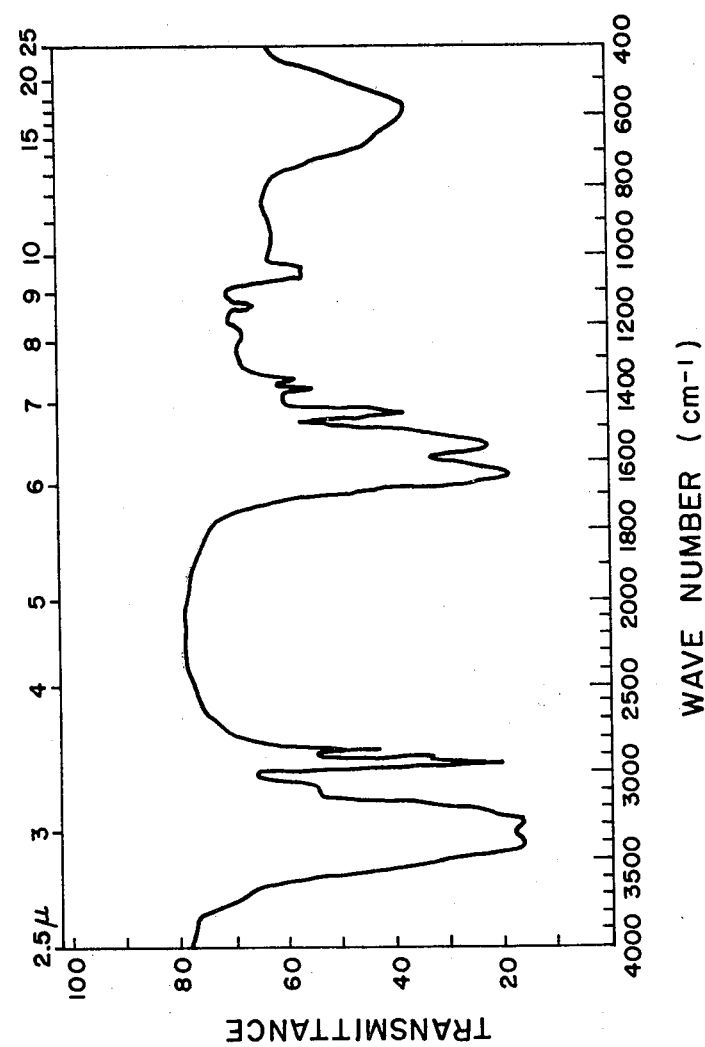

A compound of the formula (I) wherein both X and Y are L-valine (80 g) was placed in a 10-liter glass reactor together with methanol (5 liters) of 45° C., and dissolved with stirring. A 3N aqueous sodium hydroxide solution (39.0 ml) was added, and the resulting solution was cooled with ice water. Separately from this, methanol (500 ml) was taken in a 1-liter glass beaker and cooled with ice water from the outside. Anhydrous aluminum chloride (39.5 g) was gradually added thereto with stirring while continuing the cooling, and then water (122 ml) was added. This aluminum chloride/methanol/water mixed solution was gradually added to the above solution, followed by 1 hour's stirring at room temperature. A 3 N aqueous sodium hydroxide solution (234 ml) was then added dropwise with stirring to adjust the pH to 6.8, followed by standing overnight at room temperature. From the reaction solution containing precipitate was removed methanol under reduced pressure, and the solution was further concentrated to 1.5 liters. To this concentrated liquor was added water (3 liters), followed by 1 hour's stirring at room temperature for completion of gelation. Thereafter, filtration, washing and drying were carried out in the same manner as in Example 3 to obtain 95 g of a powder. This powder showed the following properties: Antacid power, 78 ml of 0.1 N HCl per gram; and pepsin inhibiting activity ($ID_{50}$), 0.055 μg. This compound had the following composition: Content of a compound derived from the compound of the formula (I), 72.4%; and aluminum content, 6.8%. FIG. 4 shows the IR spectrum of this compound.

EXAMPLE 5

Methanol (750 ml) was placed in a 2-liter glass reactor and heated to 45° C. A compound of the formula (I) wherein both X and Y are L-valine (15.0 g) was added thereto and dissolved with stirring. A 3 N aqueous sodium hydroxide solution (7.3 ml) was added to the resulting solution which was then cooled to room temperature. Further, an aqueous basic aluminum chloride solution (85 g), produced by Sumitomo Aluminum Refining Co., having an aluminum oxide content of 10.3% and a basicity (B) of 52.3% [with basic aluminum chloride of the formula, $Al_2(OH)_nCl_{6-n}$, basicity (B) is defined as $(n/6) \times 100\%$] was added thereto, and reaction was carried out for 30 minutes with stirring. This reaction solution was stirred for 1 hour, while being adjusted to a pH of 6.8 with addition of a 1 N aqueous sodium hydroxide solution (190.5 ml), to get gel-form precipitate. Thereafter, filtration, washing and drying were carried out in the same manner as in Example 3 to obtain 30.3 g of a powder.

Figure 5:
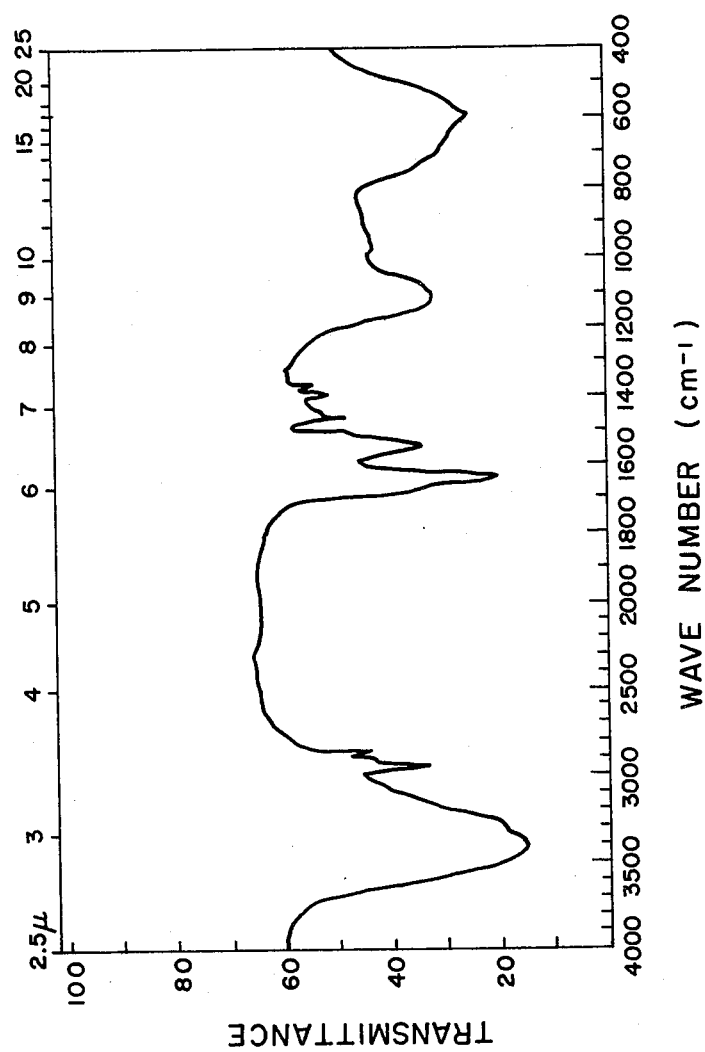

The antacid power and pepsin inhibiting activity ($ID_{50}$) of the powder were measured according to the methods of Example 1 to obtain the following results: Antacid power, 141 ml of 0.1 N HCl per gram; and $ID_{50}$, 0.07 μg. This compound had the following composition: Content of a compound derived from the compound of the formula (I), 43.5%; and aluminum content, 15.1%. FIG. 5 shows the IR spectrum of this compound.

EXAMPLE 6

Methanol (500 ml) was placed in a 2-liter glass reactor and heated to 45° C. A compound of the formula (I) wherein both X and Y are L-valine (10.9 g) was added thereto and dissolved with stirring. A 3 N aqueous sodium hydroxide solution (5.3 ml) was added to the resulting solution which was then cooled to room temperature. Further, an aqueous basic aluminum chloride solution (176.9 g) described in Example 5 was added thereto, and reaction was carried out for 30 minutes with stirring. This reaction solution was stirred for 1 hour, while being adjusted to a pH of 6.8 with addition of a 1 N aqueous sodium hydroxide solution (459.2 ml), to get gel-form precipitate. Thereafter, filtration, washing and drying were carried out in the same manner as in Example 3 to obtain 45.4 g of a powder.

Figure 6:
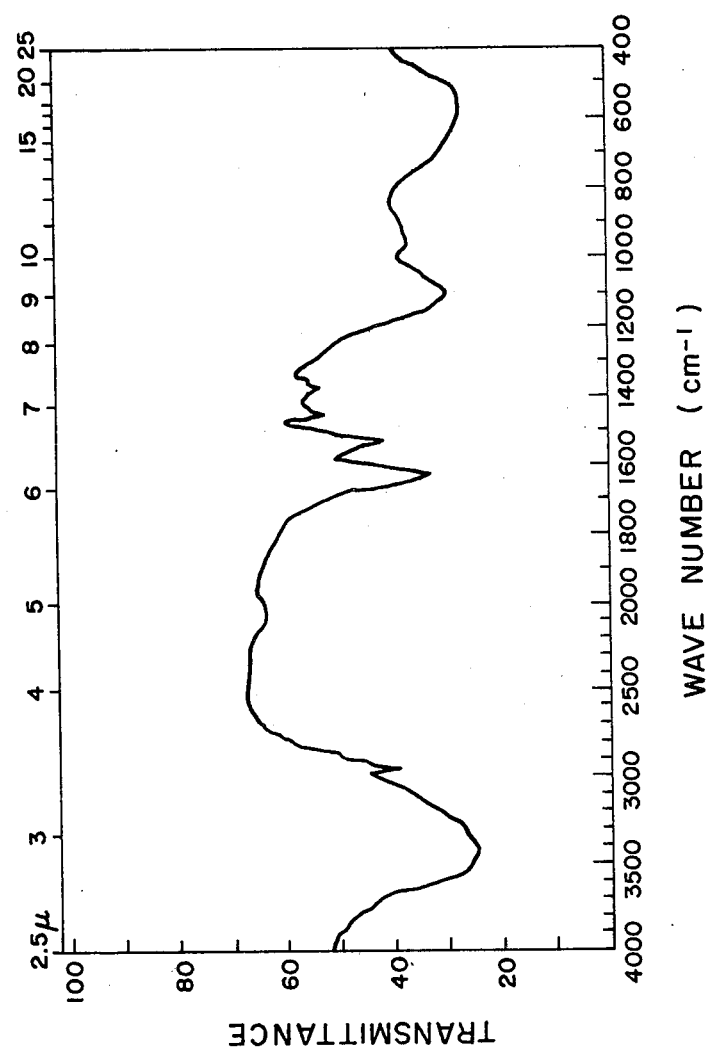

The antacid power and pepsin inhibiting activity ($ID_{50}$) of the powder were measured according to the methods of Example 1 to obtain the following results: Antacid power, 191 ml of 0.1 N HCl per gram; and $ID_{50}$, 0.09 μg. This compound had the following composition: Content of a compound derived from the compound of the formula (I), 24.6%; and aluminum content, 22.0%. FIG. 6 shows the IR spectrum of this compound.

EXAMPLE 7

Methanol (500 ml) was placed in a 2-liter glass reactor and heated to 45° C. A compound of the formula (I) wherein both X and Y are L-valine (6.5 g) was added thereto and dissolved with stirring. A 3 N aqueous sodium hydroxide solution (3.2 ml) was added to the resulting solution which was then cooled to room temperature. Further, an aqueous basic aluminum chloride solution (318.4 g) described in Example 5 was added thereto, and reaction was carried out for 30 minutes with stirring. This reaction solution was stirred for 1 hour, while being adjusted to a pH of 6.8 with addition of a 1 N aqueous sodium hydroxide solution (409.1 ml), to get gel-form precipitate. Thereafter, filtration, washing and drying were carried out in the same manner as in Example 3 to obtain 69.2 g of a powder.

Figure 7:
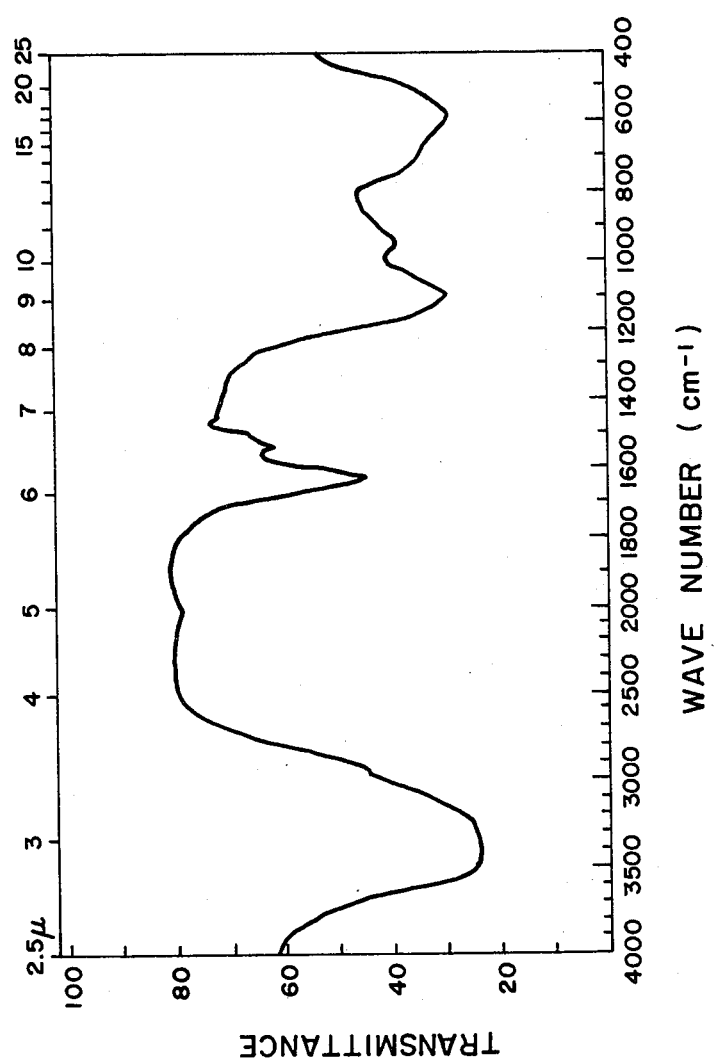

The antacid power and pepsin inhibiting activity ($ID_{50}$) of the powder were measured according to the methods of Example 1 to obtain the following results: Antacid power, 225 ml of 0.1 N HCl per gram; and ID$_{50}$, 0.10 μg. This compound had the following composition: Content of a compound derived from the compound of the formula (I), 12.5%; and aluminum content, 26.0%. FIG. 7 shows the IR spectrum of this compound.

EXAMPLE 8

The acidic protease inhibitors prepared by the methods of Examples 1 to 7 were tested for a therapeutic effect on thermocautery ulcer on rat. The thermocautery ulcer was developed according to the method described in K. Tsuji et. al., Experimental ulcer-animal model and its etiology, No. 32, pp 92 (Nippon Medical Center, Tokyo, 1976).

Ulcer was developed by opening the abdomen of rats having a body weight of 210 to 230 g and searing corpus by greater curvature. Test drugs were orally administered to the rats for 9 days from the next day. For learning the therapeutic effect of the test drugs, a curative ratio was obtained by comparison of ulcer dimensions between the control group and drug-treated group.

It is clear from Table 1 that the acidic protease inhibitors of the present invention exhibit a therapeutic effect on even experimental ulcer on which both the compound of the formula (I) and aluminum hydroxide gel have no effect.

TABLE 1

Curative effect on thermocautery ulcer

| Drug | Dosage (mg/kg) | Curative ratio* |
|---|---|---|
| Acidic protease inhibitor obtained in Example 2 | 300 | ++ |
| Acidic protease inhibitor obtained in Example 3 | 300 | ++ |
| Acidic protease inhibitor obtained in Example 4 | 300 | + |
| Acidic protease inhibitor obtained in Example 5 | 300 | ++ |
| Acidic protease inhibitor obtained in Example 6 | 300 | ++ |
| Acidic protease inhibitor obtained in Example 7 | 300 | + |
| Compound of the formula (I) (X and Y are L-valine) | 300 | — |
| 1:1 Mixture of the compound of the formula (I) and aluminum hydroxide gel | 300 | — |
| Aluminum hydroxide gel | 300 | — |

*Curative ratio
~ 10%:—
11% ~ 50%:+
51% ~ :++

EXAMPLE 9

A tablet having the following composition was produced by the usual method.

| Acidic protease inhibitor obtained in Example 1 or 2 | 300 mg |
|---|---|
| Starch | 500 mg |
| Precipitated silica | 100 mg |
| Magnesium stearate | 10 mg |

We claim:

1. An acidic protease inhibitor obtained as precipitated by allowing a compound of the formula (I),

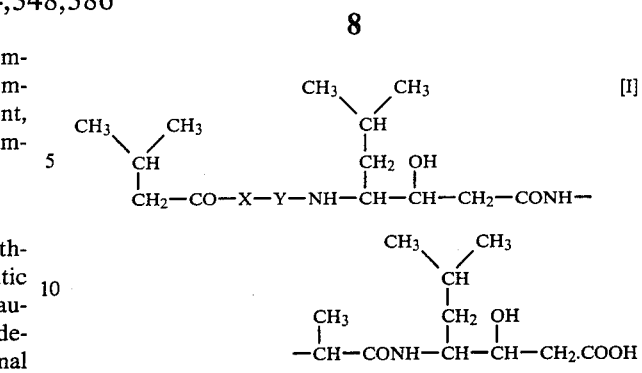

wherein X and Y are L-leucine or L-valine, or its salt to react with an aluminum compound in a medium containing water and/or an alcohol, and further continuing the reaction after adjusting the pH of the system to within a range of 4.5 to 7.

2. An acidic protease inhibitor according to claim 1, wherein the amount of the aluminum compound used is 0.05 to 20 times by weight, as converted to alumina (Al$_2$O$_3$), based on the compound of the formula (I) or its salt.

3. An acidic protease inhibitor according to claim 2, wherein the amount of the aluminum compound used is 0.1 to 10 times by weight, as converted to alumina (Al$_2$O$_3$), based on the compound of the formula (I) or its salt.

4. An acidic protease inhibitor according to claim 3, wherein the amount of the aluminum compound used is 0.1 to 5 times by weight, as converted to alumina (Al$_2$O$_3$), based on the compound of the formula (I) or its salt.

5. An acidic protease inhibitor according to claims 1 to 4, wherein the aluminum compound is a chlorinated aluminum compound or organo-aluminum compound.

6. An acidic protease inhibitor according to claim 5, wherein the chlorinated aluminum compound is aluminum chloride or basic aluminum chloride.

7. An acidic protease inhibitor according to claims 1 to 6, wherein the medium is one containing water and an alcohol.

8. An acidic protease inhibitor according to claim 7, wherein the alcohol is methanol.

9. A process for producing an acidic protease inhibitor as precipitate by allowing a compound of the formula (I),

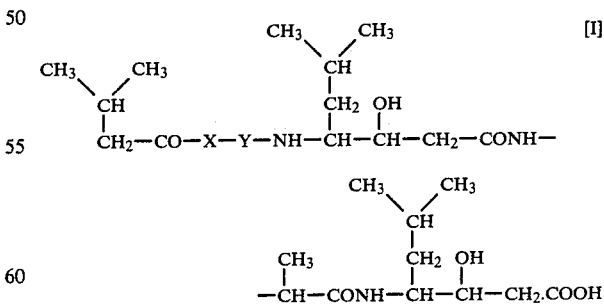

wherein X and Y are L-leucine or L-valine, or its salt to react with an aluminum compound in a medium containing water and/or an alcohol, followed by reaction at a pH of 4.5 to 7.

10. A process according to claim 9, wherein the amount of the aluminum compound used is 0.05 to 20 times by weight, as converted to alumina (Al₂O₃), based on the compound of the formula (I) or its salt.

11. A process according to claim 10, wherein the amount of the aluminum compound used is 0.1 to 10 times by weight, as converted to alumina (Al₂O₃), based on the compound of the formula (I) or its salt.

12. A process according to claim 11, wherein the amount of the aluminum compound used is 0.1 to 5 times by weight, as converted to alumina (Al₂O₃), based on the compound of the formula (I) or its salt.

13. A process according to claims 9 to 12, wherein the aluminum compound is a chlorinated aluminum compound or organo-aluminum compound.

14. A process according to claim 13, wherein the chlorinated aluminum compound is aluminum chloride or basic aluminum chloride.

15. A process according to claims 9 to 14, wherein the medium is one containing water and an alcohol.

16. A process according to claim 15, wherein the alcohol is methanol.

17. A pharmaceutical composition suitable for the treatment of chronic ulcers which comprises at least one of the acidic protease inhibitors as claimed in claim 1 as an active ingredient and a pharmaceutically acceptable carrier or diluent.

18. A pharmaceutical composition according to claim 17 having an anti-pepsin action, an antacid action and a therapeutic effect on chronic ulcers.

19. A process of treating a chronic ulcer comprising administering to a warm-blooded animal a therapeutically effective amount to treat said ulcer of an acid protease inhibitor of claim 1.

20. A process of inhibiting the action of pepsin comprising administering to a warm-blooded animal a pepsin inhibiting amount of an acid protease inhibitor of claim 1.

21. A process for administering to a warm-blooded animal an acid protease inhibitor of claim 1 in an amount effective to act as an antacid.

22. A pharmaceutical composition according to claim 17 wherein the composition contains 50 to 1000 mg of the active ingredient.

23. An acid protease inhibitor according to claim 1 wherein X and Y are both L-valine.

* * * * *